United States Patent [19]

Buzzetti et al.

[11] Patent Number: 5,436,235
[45] Date of Patent: Jul. 25, 1995

[54] 3-ARYL-GLYCIDIC ESTER DERIVATIVES

[75] Inventors: Franco Buzzetti, Monza; Maria G. Brasca, Cusago; Silvia Fustinoni; Sergio Penco, both of Milan, all of Italy

[73] Assignee: Farmitalia Carlo Erba S.r.l., Milan, Italy

[21] Appl. No.: 16,980

[22] Filed: Feb. 12, 1993

[30] Foreign Application Priority Data

Mar. 6, 1992 [GB] United Kingdom ............... 9204945

[51] Int. Cl.$^6$ ............................................. C07D 27/56
[52] U.S. Cl. ...................................... 514/92; 546/133
[58] Field of Search .......................... 546/133; 514/92

[56] References Cited

FOREIGN PATENT DOCUMENTS 1226463 3/1971 United Kingdom .

OTHER PUBLICATIONS

CA: 108:55860 (1976).
CA: 86:43883 (1960).
CA: 80:47718 (1958).
CA: 75:110163 (1956).
CA: 102:149006 (1970).
Journal of Organic Chemistry, vol. 41, No. 15 (1976), pp. 2654–2656, I. J. Lev et al.
Chemical Abstracts, vol. 105 (1986), Abstract No. 216726, Ken Kawada et al.
Journal of Natural Products, vol. 55, No. 11, Nov. 1992, pp. 1529–1560, C. Chang et al.
Chemical and Pharmaceutical Bulletin, vol. 36, No. 3 (1988), Tokyo, JP, pp. 974–981, T. Shiraishi et al.
Farmitalia Carlo Erba, WO-A-9 113 055, Sep. 5, 1991, Abstract.
Chemical Abstract, vol. 102, AN–166261k, 1985.
Journal of Organic Chemistry, vol. 28, 1963, pp. 1514–1521, C. C. Tung, et al., "The Darzens Condensation. II. Reaction of Chloroacetamides with Aromatic Aldehydes".
Indian Journal of Chemistry, vol. 10, Oct. 1972, pp. 973–976, Padam C. Jain, et al., "Stere-Selective Synthesis of Threo- & Erythro-(Beta-Naphthyl)-Serines & Erythro-(Beta-Naphthyl)-Isoserines".
Journal of Organic Chemistry, vol. 41, No. 23, 1976, pp. 3747–3752, K. Ishikawa, et al., "Photoisomerization of Selected Oxiranes.Intermediacy of Carbonyl Ylides".

*Primary Examiner*—Johann Richter
*Assistant Examiner*—Catherine S. K. Scalzo
*Attorney, Agent, or Firm*—Oblon, Spivak, McClelland, Maier & Neustadt

[57] ABSTRACT

The present invention relates to 3-aryl-oxirane derivatives of the formula

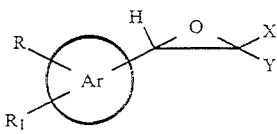

wherein Ar is 4'-quinoline or 5'-quinoline; each of R and $R_1$ independently is hydrogen or $C_1$–$C_6$ alkoxy; one of X and Y is hydrogen, cyano, —COOR$_2$ or —CONR$_3$R$_4$, and the other of X and Y is cyano, —COOR$_2$ or —CONR$_3$R$_4$, wherein R$_2$ is $C_1$–$C_6$ alkyl and each of R$_3$ and R$_4$ independently is hydrogen or $C_1$–$C_6$ alkyl, and pharmaceutically acceptable salts thereof, which are useful in therapy as tyrosine kinase inhibitors, in particular as anti-proliferative agents, typically as anti-cancer agents, in the treatment of psoriasis and in inhibiting the development of atheromatous plaque.

4 Claims, No Drawings

3-ARYL-GLYCIDIC ESTER DERIVATIVES

The present invention relates to 3-aryl-oxirane derivatives, to a process for their preparation, to pharmaceutical compositions containing them and their use as therapeutic agents, in particular as tyrosine kinase inhibitors.

3-Aryl-oxirane derivatives are known for instance from J. Org. Chem., 41(23), 3747 (1976), Indian J. Chem., 10(10), 973-6 (1972) and GB-A-1226463. In particular the former prior art reference relates to the synthesis of several α-cyano β-arylglycidates and to a study concerning their trans-cis photoisomerization. The second above reference relates to the stereoselective synthesis of threo- and erythro-(β-naphthyl) serines and erythro-(β-naphthyl) isoserines. GB-A-1226463 discloses 1,3,5-trisubstituted- and 1,2,3,5-tetrasubstituted-indole derivatives, having activity as anti-inflammatory and antipyretic agents.

As a first object the present invention provides compounds having the general formula (I)

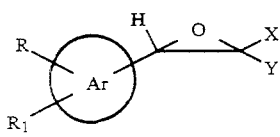

wherein
Ar is a bicyclic ring system chosen from naphthalene, 5', 6', 7', 8'-tetrahydronaphthalene, quinoline and indole;
each of R and $R_1$ independently is hydrogen or a substituent chosen from halogen, hydroxy, $C_1$-$C_6$ alkyl, $C_1$-$C_6$ alkoxy, $C_2$-$C_6$ acyloxy, cyano and nitro;
one of X and Y is hydrogen, cyano or a —$COOR_2$ or —$CONR_3R_4$ group, in which $R_2$ is $C_1$-$C_6$ alkyl and each of $R_3$ and $R_4$ independently is hydrogen or $C_1$-$C_6$ alkyl, and the other independently is cyano or a —$COOR_2$ or —$CONR_3R_4$ group, wherein $R_2$, $R_3$ and $R_4$ are as defined above, for use as an active therapeutic substance, in particular as tyrosine kinase inhibitor.

A further object of the present invention is to provide a pharmaceutical composition comprising a pharmaceutically acceptable carrier and/or diluent and, as an active principle, a compound of formula (I), as defined above.

Object of the present invention is also the use of a compound of formula (I), as defined above, for the manufacture of a medicament for use as tyrosine kinase inhibitor, in particular as anti-cancer and anti-proliferative agent.

The compounds of formula (I) above are new with the exception of some 3-naphthyl- and 3-indolyl-oxirane derivatives which are disclosed by the above-mentioned prior art references. However, no therapeutic utility is disclosed for said known compounds in said prior art references. Both the new and the known compounds of general formula (I) are hereafter referred to as the "active compounds" and as the "compounds of the invention".

Compounds falling within the scope of general formula (I) above are all the possible isomers, stereoisomers, in particular cis- and trans-isomers and their mixtures, and the metabolites and the metabolic precursors or bio-precursors (otherwise known as pro-drugs) of the compounds of formula (I).

The alkyl groups and the alkyl moieties in the alkoxy and acyloxy groups may be branched or straight chains.

A $C_1$-$C_6$ alkyl group is preferably a $C_1$-$C_4$ alkyl group, e.g. methyl, ethyl, propyl, isopropyl, butyl, sec-butyl or tert-butyl, in particular methyl or ethyl.

A $C_1$-$C_6$ alkoxy group is preferably a $C_1$-$C_4$ alkoxy group, e.g. methoxy, ethoxy, propoxy, isopropoxy, butoxy, sec-butoxy or tert-butoxy, in particular methoxy.

A $C_2$-$C_6$ acyloxy group is preferably a $C_2$-$C_3$ acyloxy group, in particular an acetoxy or propionyloxy.

A halogen is preferably fluorine, chlorine or bromine, in particular chlorine.

Each of the substituents R, $R_1$ and the epoxy group may be independently on either of the aryl or heteroaryl moieties of the Ar group where Ar denotes naphthalene, quinoline or indole. Only the benzene moiety is preferably substituted when Ar is a 5', 6', 7', 8'-tetrahydronaphthalene group. Preferred substitution patterns are as follows:

(i) When Ar is naphthalene, the R and $R_1$ groups and the epoxy group are preferably on the same benzene Preferably the naphthyl group is a 1'-naphthyl or group. When the 1'-naphthyl group is substituted, preferably at the 4'-position. When the 2'-naphthyl group substituted, R or $R_1$ is preferably at the 1'-position.

(ii) When Ar is 5', 6', 7', 8'-tetrahydronaphthalene, it is preferably linked at the 1'- or 2'-position to the epoxy group. When the 1'-linked group substituted, R or $R_1$ is preferably at the 4'-position. When the 2'-linked group is substituted, R or $R_1$ is preferably at the 1'-position.

(iii) When Ar is quinoline, the epoxy group is preferably attached to the 4'- or 5'-position of the quinolyl group, and R and $R_1$ are preferably on the benzene moiety of said condensed ring system. When the 4'-quinolyl and the 5'-quinolyl groups are substituted, R or $R_1$ is preferably at the 8'-position.

(iv) When Ar is indole, the epoxy group is preferably attached to the heteroaryl moiety and R and $R_1$ are preferably on the benzene moiety, of said condensed ring system. Preferably, Ar is a 3'-indolyl group. When the 3'-indolyl group is substituted, R or $R_1$ is preferably at the 5'-position.

Of course only one of the substituents i.e. the R, $R_1$ and the epoxy group can be linked to the same carbon atom of the Ar mono- or bicyclic ring system.

When one of X and Y is a CN, $COOR_2$ or $CONR_3R_4$ group as defined above, then the other has preferably a different meaning.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I). Preferred compounds for use as active therapeutic substances or as active ingredients in the preparation of a pharmaceutical composition, according to the invention, are the compounds of formula (I), wherein Ar is as defined above;
R is hydrogen, hydroxy or $C_1$-$C_6$ alkoxy;

R₁ is hydrogen;
one of X and Y is —CN, —COOR₂ or —CONR₃R₄, in which R₂ is C₁–C₄ alkyl and each of R₃ and R₄ independently is hydrogen or C₁–C₄ alkyl, and the other is hydrogen or CN.

More preferred compounds for use as active therapeutic substances or as active ingredients in the preparation of a pharmaceutical composition, according to the invention, are the compounds of formula (I), wherein
Ar is as defined above;
R is hydrogen or C₁–C₆ alkoxy;
R is hydrogen;
one of X and Y is —COOR₂ or —CONR₃R₄, in which R₂ is C₁–C₄ alkyl and each of R₃ and R₄ independently is hydrogen or C₁–C₄ alkyl, and the other is hydrogen or cyano.

Examples of specific preferred compounds of the invention for use as active therapeutic substances or as active ingredients in the preparation of a pharmaceutical composition according to the invention are the following:
2-carbethoxy-3-(1'-naphthyl)oxirane;
2-carbamoyl-3-(1'-naphthyl)oxirane;
2-cyano-3-(1'-naphthyl)oxirane;
2-cyano-2-carbethoxy-3-(1'-naphthyl)oxirane;
2-cyano-2-carbamoyl -8-(1'-naphthyl)oxirane;
2-carbethoxy-3-(4'-methoxy-1'-naphthyl)oxirane;
2-carbamoyl -3-(4'-methoxy-1'-naphthyl)oxirane;
2-cyano-3-(4'-methoxy-1'-naphthyl)oxirane;
2-cyano-2-carbethoxy-3-(4'-methoxy-1'-naphthyl)oxirane
2-cyano-2-carbamoyl-3-(4'-methoxy-1'-naphthyl)oxirane;
2-carbethoxy-3-(2'-naphthyl)oxirane:
2-carbamoyl-3-(2'-naphthyl)oxirane;
2-cyano-3-(2'-naphthyl)oxirane;
2-cyano-2-carbethoxy-3-(2'-naphthyl)oxirane;
2-cyano-2-carbamoyl -3-(2'-naphthyl)oxirane;
2-carbethoxy-3-(1'-methoxy-2'-naphthyl)oxirane;
2-carbamoyl-3-(1'-methoxy-2'-naphthyl)oxirane;
2-cyano-3-(1'-methoxy-2'-naphthyl)oxirane;
2-cyano-2-carbethoxy-3-(1'-methoxy-2'-naphthyl)oxirane
2-cyano-2-carbamoyl-3-(1'-methoxy-2'-naphthyl)oxirane;
2-carbethoxy-3-(5', 6', 7', 8'-tetrahydronaphth-1'-yl) oxirane;
2-carbamoyl-3-(5', 6', 7', 8'-tetrahydronaphth-1'-yl)oxirane;
2-cyano-3-(5', 6', 7', 8'-tetrahydronaphth-1'-yl)oxirane;
2-cyano-2-carbethoxy-8-(5', 6', 7', 8'-tetrahydronaphth-1'-yl)oxirane;
2-cyano-2-carbamoyl-8-(5', 6', 7', 8'-tetrahydronaphth-1'-yl)oxirane;
2-carbethoxy-8-(4'-methoxy-5', 6', 7', 8'-tetrahydronaphth-1'-yl)oxirane;
2-carbamoyl-8-(4'-methoxy-5', 6', 7', 8'-tetrahydronaphth-1'-yl)oxirane;
2-cyano-8-(4'-methoxy-5', 6', 7', 8'-tetrahydronaphth-1'-yl)oxirane;
2-cyano-2-carbethoxy-3-(4'-methoxy-5', 6', 7', 8'-tetrahydronaphth-1'-yl)oxirane;
2-cyano-2-carbamoyl-8-(4'-methoxy-5', 6', 7', 8'-tetrahydronaphth-1'-yl)oxirane;
2-carbethoxy-3-(5', 6', 7', 8'-tetrahydronaphth-2'-yl)oxirane;
2-carbamoyl-8-(5', 6', 7', 8'-tetrahydronaphth-2'-yl)oxirane;
2-cyano-8-(5', 6', 7', 8'-tetrahydronaphth-2'-yl)oxirane;
2-cyano-2-carbethoxy-3-(5', 6', 7', 8'-tetrahydronaphth-2'-yl)oxirane;
2-cyano-2-carbamoyl-8-(5', 6', 7', 8'-tetrahydronaphth-2'-yl)oxirane;
2-carbethoxy-8-(1'-methoxy-5', 6', 7', 8'-tetrahydronaphth2'-yl)oxirane;
2-carbamoyl-3-(1'-methoxy-5', 6', 7', 8'-tetrahydronaphth-2'-yl)oxirane;
2-cyano-8-(1'-methoxy-5', 6', 7', 8'-tetrahydronaphth-2'-yl) oxirane;
2-cyano-2-carbethoxy-3-(1'-methoxy-5', 6', 7', 8'-tetrahydronaphth-2'-yl)oxirane;
2-cyano-2-carbamoyl-3-(1'-methoxy-5', 6', 7', 8'-tetrahydronaphth-2'-yl)oxirane;
2-carbethoxy-8-(4'-quinolyl)oxirane;
2-carbamoyl-3-(4'-quinolyl)oxirane;
2-cyano-3-(4'-quinolyl)oxirane;
2-cyano-2-carbethoxy-3-(4'-quinolyl)oxirane;
2-cyano-2-carbamoyl -3-(4'-quinolyl)oxirane;
2-carbethoxy-3-(8'-methoxy-4'-quinolyl)oxirane;
2-carbamoyl-3-(8'-methoxy-4'-quinolyl)oxirane;
2-cyano-3-(8'-methoxy-4'-quinolyl)oxirane;
2-cyano-2-carbethoxy-3-(8'-methoxy-4'-quinolyl)oxirane;
2-cyano-2-carbamoyl-3-(8'-methoxy-4'-quinolyl)oxirane;
2-carbethoxy-3-(5'-quinolyl)oxirane;
2-carbamoyl-3-(5'-quinolyl)oxirane;
2-cyano-3-(5'-quinolyl)oxirane;
2-cyano-2-carbethoxy-3-(5'-quinolyl)oxirane;
2-cyano-2-carbamoyl -3-(5'-quinolyl)oxirane;
2-carbethoxy-3-(8'-methoxy-5'-quinolyl)oxirane;
2-carbamoyl-3-(8'-methoxy-5'-quinolyl)oxirane;
2-cyano-3-(8'-methoxy-5'-quinolyl)oxirane;
2-cyano-2-carbethoxy-3-(8'-methoxy-5'-quinolyl)oxirane;
2-cyano-2-carbamoyl -3-(8'-methoxy-5'-quinolyl)oxirane;
2-carbethoxy-3-(3'-indolyl)oxirane;
2-carbamoyl-3-(3'-indolyl)oxirane;
2-cyano-3-(3'-indolyl)oxirane;
2-cyano-2-carbethoxy-3-(3'-indolyl)oxirane;
2-cyano-2-carbamoyl-3-(3'-indolyl)oxirane;
2-carbethoxy-3-(3'-methoxy-3'-indolyl)oxirane;
2-carbamoyl-3-(3'-methoxy-3'-indolyl)oxirane;
2-cyano-3-(3'-methoxy-3'-indolyl)oxirane;
2-cyano-2-carbethoxy-3-(5'-methoxy-3'-indolyl)oxirane; and
2-cyano-2-carbamoyl-3-(5'-methoxy-3'-indolyl)oxirane;
which, when appropriate, may be either cis- or trans-diastereomers or cis,trans-mixtures of said diastereomers.

An object of the present invention is also to provide new 3-aryl-oxirane derivatives, which are encompassed by formula (I) above and have the following formula (IA)

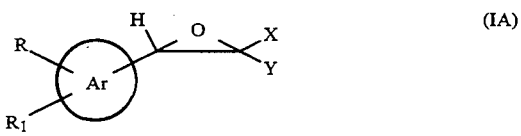
(IA)

wherein

Ar is a bicyclic ring system chosen from naphthalene, 5', 6', 7', 8'-tetrahydronaphthalene, quinoline and indole;

each of R and $R_1$ independently is hydrogen or a substituent chosen from halogen, hydroxy, $C_1$–$C_6$ alkyl, $C_1$–$C_6$ alkoxy, $C_2$–$C_6$ acyloxy, cyano and nitro;

one of X and Y is hydrogen, cyano or a —$COOR_2$ or —$CONR_3R_4$ group, in which $R_2$ is $C_1$–$C_6$ alkyl and each of $R_3$ and $R_4$ independently is hydrogen or $C_1$–$C_6$ alkyl, and the other independently is cyano or a —$COOR_2$ or —$CONR_3R_4$ group, wherein $R_2$, $R_3$ and $R_4$ are as defined above; and wherein (a) when the —(Ar)$RR_1$ group represents unsubstituted 2'-naphthyl and at the same time one of X and Y is —$COOCH_3$ then the other is other than hydrogen or cyano, and wherein (b) when the —(Ar)$RR_1$ group represents a

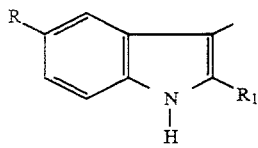

group in which R is $C_1$–$C_6$ alkyl or $C_1$–$C_6$ alkoxy and $R_1$ is hydrogen or $C_1$–$C_6$ alkyl, and at the same time one of X and Y is —$COOR_2$ in which $R_2$ is $C_1$–$C_6$ alkyl, then the other is other than hydrogen, and wherein (c) when the (Ar)$RR_1$ group represents unsubstituted 2-naphthyl and at the same time one of X and Y is cyano then the other is other than cyano.

Preferred classes of compounds of formula (IA) are, subject to the above proviso, the preferred types of compounds of formula (I). A preferred class of new compounds according to the present invention are therefore the compounds of formula (IA), wherein, subject to the above proviso:

Ar is as defined above;
R is hydrogen, hydroxy or $C_1$–$C_6$ alkoxy;
R is hydrogen;
one of X and Y is —CN —$COOR_2$ or —$CONR_3R_4$, in which $R_2$ is $C_1$–$C_4$ alkyl and each of $R_3$ and $R_4$ independently is hydrogen or $C_1$–$C_4$ alkyl, and the other is hydrogen or CN.

More preferred new compounds of formula (IA) are those wherein, subject to the above proviso:

Ar is as defined above;
R is hydrogen or $C_1$–$C_6$ alkoxy;
$R_1$ is hydrogen;
one of X and Y is —$COOR_2$ or —$CONR_3R_4$, in which $R_2$ is $C_1$–$C_4$ alkyl and each of $R_3$ and $R_4$ independently is hydrogen or $C_1$–$C_4$ alkyl, and the other is hydrogen or cyano.

Preferred examples of new compounds of formula (IA) provided by the present invention are the following:

2-carbethoxy-3-(1'-naphthyl)oxirane;
2-carbamoyl-3-(1'-naphthyl)oxirane;
2-cyano-3-(1'-naphthyl)oxirane;
2-cyano-2-carbethoxy-3-(1'-naphthyl)oxirane;
2-cyano-2-carbamoyl-3-(1'-naphthyl)oxirane;
2-carbethoxy-3-(4'-methoxy-1'-naphthyl)oxirane;
2-carbamoyl-3-(4'-methoxy-1'-naphthyl)oxirane;
2-cyano-3-(4'-methoxy-1'-naphthyl)oxirane;
2-cyano-2-carbethoxy-3-(4'-methoxy-1'-naphthyl)oxirane;
2-cyano-2-carbamoyl-3-(4'-methoxy-1'-naphthyl)oxirane;
2-carbethoxy-3-(2'-naphthyl)oxirane;
2-carbamoyl-3-(2'-naphthyl)oxirane;
2-cyano-3-(2'-naphthyl)oxirane;
2-cyano-2-carbethoxy-3-(2'-naphthyl)oxirane;
2-cyano-2-carbamoyl-3-(2'-naphthyl)oxirane;
2-carbethoxy-3-(1'-methoxy-2'-naphthyl)oxirane;
2-carbamoyl-3-(1'-methoxy-2'-naphthyl)oxirane;
2-cyano-3-(1'-methoxy-2'-naphthyl)oxirane;
2-cyano-2-carbethoxy-3-(1'-methoxy-2'-naphthyl)oxirane;
2-cyano-2-carbamoyl-3-(1'-methoxy-2'-naphthyl)oxirane;
2-carbethoxy-3-(5', 6', 7', 8'-tetrahydronaphth-1'-yl)oxirane;
2-carbamoyl-3-(5', 6', 7', 8'-tetrahydronaphth-1'-yl)oxirane;
2-cyano-3-(5', 6', 7', 8'-tetrahydronaphth-1'-yl)oxirane;
2-cyano-2-carbethoxy-3-(5', 6', 7', 8'-tetrahydronaphth-1'-yl)oxirane;
2-cyano-2-carbamoyl-3-(5', 6', 7', 8'-tetrahydronaphth-1'-yl)oxirane;
2-carbethoxy-3-(4'-methoxy-5', 6', 7', 8'-tetrahydronaphth-1'-yl)oxirane;
2-carbamoyl-3-(4'-methoxy-5', 6', 7', 8'-tetrahydronaphth-1'-yl)oxirane;
2-cyano-3-(4'-methoxy-5', 6', 7', 8'-tetrahydronaphth-1'-yl)oxirane;
2-cyano-2-carbethoxy-3-(4'-methoxy-5', 6', 7', 8'-tetrahydronaphth-1'-yl)oxirane;
2-cyano-2-carbamoyl-3-(4'-methoxy-5', 6', 7', 8'-tetrahydronaphth-1'-yl)oxirane;
2-carbethoxy-3-(5', 6', 7', 8'-tetrahydronaphth-2'-yl)oxirane;
2-carbamoyl-3-(5', 6', 7', 8'-tetrahydronaphth-2'-yl)oxirane;
2-cyano-3-(5', 6', 7', 8'-tetrahydronaphth-2'-yl)oxirane;
2-cyano-2-carbethoxy-3-(5', 6', 7', 8'-tetrahydronaphth-2'-yl)oxirane;
2-cyano-2-carbamoyl-3-(5', 6', 7', 8'-tetrahydronaphth-2'-yl)oxirane;
2-carbethoxy-3-(1'-methoxy-5', 6', 7', 8'-tetrahydronaphth-2'-yl)oxirane;
2-carbamoyl-3-(1'-methoxy-5', 6', 7', 8'-tetrahydronaphth-2'-yl)oxirane;
2-cyano-3-(1'-methoxy-5', 6', 7', 8'-tetrahydronaphth-2'-yl)oxirane;
2-cyano-2-carbethoxy-3-(1'-methoxy-5', 6', 7', 8'-tetrahydronaphth-2'-yl)oxirane;
2-cyano-2-carbamoyl-3-(1'-methoxy-5', 6', 7', 8'-tetrahydronaphth-2'-yl)oxirane;
2-carbethoxy-3-(4'-quinolyl)oxirane;
2-carbamoyl-3-(4'-quinolyl)oxirane;
2-cyano-3-(4'-quinolyl)oxirane;
2-cyano-2-carbethoxy-3-(4'-quinolyl)oxirane;
2-cyano-2-carbamoyl-3-(4'-quinolyl)oxirane;
2-carbethoxy-3-(8'-methoxy-4'-quinolyl)oxirane;
2-carbamoyl-3-(8'-methoxy-4'-quinolyl)oxirane;
2-cyano-3-(8'-methoxy-4'-quinolyl)oxirane;
2-cyano-2-carbethoxy-3-(8'-methoxy-4'-quinolyl)oxirane;
2-cyano-2-carbamoyl-3-(8'-methoxy-4'-quinolyl)oxirane;
2-carbethoxy-3-(3'-quinolyl)oxirane;
2-carbamoyl-3-(3'-quinolyl)oxirane;

2-cyano-3-(5'-quinolyl)oxirane;
2-cyano-2-carbethoxy-3-(5'-quinolyl)oxirane;
2-cyano-2-carbamoyl-3-(5'-quinolyl)oxirane;
2-carbethoxy-3-(8'-methoxy-5'-quinolyl)oxirane;
2-carbamoyl-3-(8'-methoxy-5'-quinolyl)oxirane;
2-cyano-3-(8'-methoxy-5'-quinolyl)oxirane;
2-cyano-2-carbethoxy-3-(8'-methoxy-5'-quinolyl)oxirane;
2-cyano-2-carbamoyl-3-(8'-methoxy-5'-quinolyl)oxirane:
2-carbethoxy-3-(8'-indolyl)oxirane;
2-carbamoyl-3-(3'-indolyl)oxirane;
2-cyano-3-(3'-indolyl)oxirane;
2-cyano-2-carbethoxy-3-(3'-indolyl)oxirane;
2-cyano-2-carbamoyl -3-(3'-indolyl)oxirane;
2-carbamoyl-3-(5'-methoxy-3'-indolyl)oxirane;
2-cyano-3-(5'-methoxy-3'-indolyl)oxirane;
2-cyano-2-carbethoxy-3-(5'-methoxy-3'-indolyl)oxirane; and
2-cyano-2-carbamoyl-3-(5'-methoxy-3'-indolyl)oxirane:
which, when appropriate, may be either cis- or trans-diastereomers or cis, trans-mixtures of said diastereomers.

Object of the instant invention is also to provide the new compound of formula (IB), which is encompassed by formula (T) above,

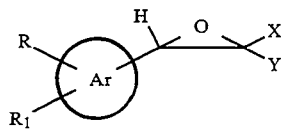  (IB)

wherein
the —(Ar) RR$_1$ group represents

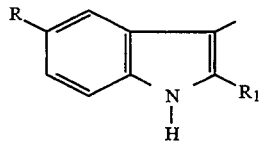

in which
R is methoxy and R is hydrogen;
one of X and Y is hydrogen and the other is —COOC$_2$H$_5$; either as cis- or trans-diastereoisomer or cis,trans-mixtures of said isomers.

The new compound of formula (IB), namely 2-carbethoxy-3(5'-methoxy-3'-indolyl)oxirane, is disclosed in general terms by GB-A-1222463, but therein not specifically mentioned as a chemical entity.

The compounds of formula (IA) and (IB) wherein the substituents Ar, R, R$_1$, X and Y, subject to the above proviso, are as herein defined, can be obtained by a process comprising:
a) condensing a compound of formula (II)

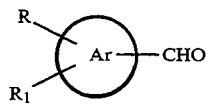  (II)

wherein Ar, R and R$_1$ are as defined above, with a compound of formula (III)

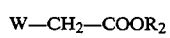  (III)

wherein W is halogen and R$_2$ is as defined above, thus obtaining a compound of the invention wherein one of X and Y is hydrogen and the other is —COOR$_2$, in which R$_2$ is as defined above, and Ar, R and R$_1$ are as defined above; or b) condensing a compound of formula (II) as defined above, with a compound of formula (IV)

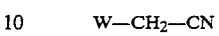  (IV)

wherein W is halogen, thus obtaining a compound of the invention wherein one of X and Y is hydrogen and the other is —CN, and Ar, R and R$_1$ are as defined above; or c) condensing a compound of formula (II), as defined above, with a compound of formula (V)

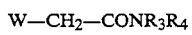  (V)

wherein W, R$_3$ and R$_4$ are as defined above, thus obtaining a compound of the invention wherein one of X and Y is hydrogen and the other is —CONR$_3$R$_4$, in which R$_3$ and R$_4$ are as defined above, and Ar, R and R$_1$ are as defined above; or d) epoxidation of a compound of formula (VI)

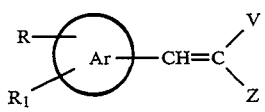  (VI)

wherein Ar, R and R$_1$ are as defined above and each of V and Z independently is cyano, —COOR$_2$ or —CONR$_3$R$_4$ in which R$_2$, R$_3$ and R$_4$ are as defined above, thus obtaining a compound of the invention wherein each of X and Y independently is cyano, —COOR$_2$ or —CONR$_3$R$_4$ in which R$_2$, R$_3$ and R$_4$ are as defined above, and, if desired, converting a compound of the invention into another compound of the invention, and/or, if desired separating a mixture of isomers of a compound of the invention into the single isomers.

In a compound of formula (III), (IV) and (V) the halogen W may be e.g. chlorine or bromine, in particular chlorine. The condensation reaction of an aldehyde of formula (II) with a compound of formula (III), (IV) or (V) may be carried out under the general conditions of the Darzens condensation.

For example the condensation of the aldehyde of formula (II) with the haloester of formula (III) may be performed as described by M. S. Newman in Organic Reactions 5, 413 (1949). Accordingly, the reaction can be carried out in an inert organic solvent, under anhydrous conditions, under an inert atmosphere, in the presence of a condensing agent and using preferably an excess of haloester, It has been found advantageous to use 1.6 moles of chlorester and 1.6 moles of alkoxide to 1 mole of aldehyde, During the first stage of the reaction low temperatures as about −76° C. are recommended which are then raised to room temperature. The most frequently used condensing agents are sodium ethoxide and sodium amide. For example the following inert solvents can be applied: ether, tetrahydrofuran or benzene.

The condensation of the aldehyde of formula (II) with the chloroacetonitrile of formula (IV) may be carried out, e.g. by the method of G. Storke et al. (J.

Am. Chem. Soc. 1960, 82, 4315). Accordingly the most generally applicable conditions involve the use of an alkali metal alkoxide, in particular potassium t-butoxide as base and a lower alkanol, e.g. t-butanol as solvent at temperatures ranging from about 0° C. to about room temperature.

Reactants and condensing agent are applied in about molar ratio. As we found this condensation may be performed advantageously also in tetrahydrofuran solution with potassium t-butoxide base at temperatures ranging from about −78° C. to room temperature and using equimolar quantities of reactants.

The condensation of an aldehyde of formula (II) with a α-chloroacetamide of formula (V) may be carried out e.g. as described by C. C. Tung et al. in J. Org. Chem. 1963, 28, 1514. Accordingly the Darzens condensation occurs in a lower alkanol, in particular t-butanol, as solvent, and with an alkali metal alkoxide, e.g. potassium t-butoxide, as base at temperatures between about 0° C. and room temperature.

The epoxidation of an acrylic compound of formula (VI) can be carried out by well known procedures e.g. by the method of Foucaud et al. (Bull. Soc. Chim. Fr. 1969, 2531). Accordingly the epoxidation can be performed with sodium hypochlorite in hydroalcoholic solution at temperatures ranging from about 0° to about 50° C. Diluted sulfuric acid can be added dropwise in order to maintain a neutral pH. Under this conditions an eventually present nitril group remains unaffected.—Alternatively the epoxidation may be carried out in the usual way with hydrogen peroxide under controlled conditions and especially avoiding a strong alkaline medium. Preferably the reaction is performed in alcohol solution such as methanol or ethanol, at temperatures ranging from about 0° to about 40° C. in the presence of a buffer of pH 7–8. Under controlled conditions there is no oxidation of the cyano group to an amide function.

A compound of the invention can be converted into another compound of the invention according to known methods, For example the de-etherification of a compound, wherein one or both of R and $R_1$ is $C_1$-$C_6$ alkoxy, so as to obtain a compound of the invention wherein one or both of R and $R_1$ is hydroxy, may be performed by well known methods in organic chemistry. For instance, in the case of a phenolic methyl ether the cleavage can be carried out for example with boron tribromide as described by J. F. N. McOmie in Tetrahedron 24, 2289 (1968). It is, in general, advisable to use about 1 mole of boron tribromide for each ether group together with an extra mole of reagent for each group containing a potentially basic group. The reaction may be performed in an inert organic solvent such as dichloromethane, pentane or benzene under an inert atmosphere, e.g. nitrogen, at temperatures ranging from about −78° C. to about 25° C. The acylation of a compound of the invention, wherein R or $R_1$ or both are hydroxy, so as to obtain a compound of the invention, wherein R or $R_1$ or both are acyloxy may be performed e.g. by reaction with a reactive derivative of a suitable carboxylic acid, such as an anhydride or halide, in the presence of a basic agent at temperatures ranging from about 0° C. to about 50° C. Preferably the acylation is carried out by reaction with the respective anhydride in the presence of an organic base such as pyridine.

The optional separation of a mixture of isomers of a compound of the invention into the single isomers may be carried out by conventional methods. For example the separation of a mixture of geometric isomers, e.g. cis- and trans-isomers, may be carried out by fractional crystallization from a suitable solvent or by chromatography, either column chromatography or high pressure liquid chromatography.

The compounds of formula (II), (III), (IV) and (V) are known or can be obtained by methods well known in the art. A compound of formula (VI) can be obtained by condensing an aldehyde of formula (II), as defined above with a compound of formula (VII)

$$Z-CH_2-V \qquad (VII)$$

wherein each of V and Z independently is cyano, $-COOR_2$ or $-CONR_3R_4$, in which $R_2$, $R_3$ and $R_4$ are as defined above under the conditions of the Knoevenagel reaction as described e.g. by G. Jones in Organic Reactions 15, 204 (1967). The condensation may be performed in an inert organic solvent e.g. pyridine, methanol, ethanol, benzene or dioxane in the presence of a suitable basic catalyst such as pyridine, piperidine or diethylamine at temperatures ranging from about 0° C. to about 100° C. Preferably the reaction is conducted in hot ethanol solution in the presence of piperidine catalyst.

When in the new compounds of the present invention and in the intermediate products thereof groups are present, which need to be protected before submitting them to the hereabove illustrated reactions, they may be protected before the reaction takes place and then deprotected at the end of the reaction, according to well known methods in organic chemistry.

PHARMACOLOGY

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence the compounds according to the present invention can be useful in the treatment of pathological proliferation disorders in mammals, including humans. Typical examples of such disorders are tumors, including leukemia, and psoriasis. They can also be useful in inhibiting the development of the atheromatous plaque. Typical therapeutical indications according to the latter use are reocclusion following coronary angioplasty and in general decrease of coronary artery disease.

Recent studies on the molecular basis of neoplastic transformation have identified a family of genes, designed oncogens, whose aberrant expression causes tumorigenesis. For example, the RNA tumor viruses possess such an oncogen sequence whose expression determines neoplastic conversion of infected cells. Several of their oncogene-encoded proteins, such as pp60$^{v-src}$, p70$^{gag-yes}$, p130$^{gag-fps}$, and P70$^{gag-fgr}$ display protein tyrosine kinase activity, that is they catalyse the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity. Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinases can be useful in investigating the mechanism of carcinogenesis, cell proliferation and differentiation and it can be effective in prevention and chemotherapy of cancer and in other pathological proliferative conditions.

The tyrosine specific protein kinase activity of these compounds is shown, e.g. by the fact that they are active in the in vitro test described by B. Ferguson et al., in J. Biol. Chem. 1985, 260, 3652.

The enzyme used is the Abelson tyrosine kinase $p60^{v\text{-}abl}$. Its production and isolation is performed according to a modification of the method of B. Ferguson et al. (ibidem). As substrate α-casein or (Val$^5$)-angiotensin II is used. The inhibitor is preincubated with the enzyme for 5 min at 25° C. The reaction conditions are:

100 mM MOPS buffer, 10 mM $MgCl_2$, 2 μM (γ-$^{32}$p) ATP (6 Ci/mmol), 1 mg/ml α-casein [an alternative substrate is (Val$^5$) angiotensin II] and 7.5 μg/ml of enzyme in a total volume of 30 μl and pH 7.0.

The reaction is incubated for 10 min at 25° C.

Trichloroacetic acid precipitation of protein is followed by rapid filtration and quantification of phosphorylated substrate by a liquid scintillation counter. Alternatively, the reaction mixture is subjected to sodium dodecyl sulfate—polyacrylamide electrophoresis and the phosphorylated substrate measured by autoradiography or $P^{32}$-counting of the excised spot.

In view of their high activity and low toxicity, the compounds of the invention can be used safely in medicine. For example, the approximate acute toxicity ($LD_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar or film-coated tablets, liquid solutions or suspensions; rectally, in the form of suppositories; parenterally, e.g. intramuscularly, or by intravenous injection or infusion; or topically. The dosage depends on the age, weight, conditions of the patient and administration route; for example, the dosage adopted for oral administration to adult humans may range from about 10 to about 150–200 mg per dose, from 1 to 5 times daily. Of course, these dosage regimens may be adjusted to provide the optimal therapeutic response. The invention includes pharmaceutical compositions comprising a compound of formula (IA) or (IB) in association with a pharmaceutically acceptable excipient (which can be a carrier or diluent).

Object of the present invention is also the use of a compound of formula (IA) or (IB), as defined above, for the manufacture of a medicament for use as tyrosine kinase inhibitor, in particular as anti-cancer and antiproliferative agent. The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginares or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be, e.g. syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or, preferably, they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin. Compositions for topical application, e.g. creams, lotions, or pastes, can be prepared by admixing the active ingredient with a conventional oleaginous or emulsifying excipient.

A further object of the present invention is a combined method of treatment of cancer in mammals, including humans, in need of such treatment, said method comprising administering 1.) a compound of formula (i), as defined above, and 2) an additional antitumor agent, in amounts and close enough together in time sufficient to produce a therapeutically useful effect.

Object of the present invention is also to provide products containing a compound of formula (I) and an additional antitumor agent as a combined preparation for simultaneous, separate or sequential use in anti-cancer therapy.

The term "antitumor agent" is meant to comprise both a single anti tumor drug and "cocktails" i.e. a mixture of such drugs, according to the clinical practice. Anti tumor agents that can be formulated with a compound of the invention or, alternatively, can be administered in a combined method of treatment, are e.g. doxorubicin, daunomycin, epirubicin, idarubicin, etoposide, fluorouracil, mephalan, cyclophosphamide, bleomycin, vinblastin and mitomycin or a mixture of two or more thereof. The compounds of the invention can therefore be used in a treatment to ameliorate a cancer. They may be administered to a patient suffering from a cancer treatable with an antitumor agent, for example an anthracycline glycoside such as doxorubicin, daunomycin, epirubicin or idarubicin as mentioned above, together with the anti-tumor agent.

A compound of the invention and an antitumor agent such as an anthracycline glycoside can be administered to improve the condition of a patient having a leukaemia such as myeloblastic leukaemia, lymphoma, sarcoma, neuroblasroma, Wilm's tumor or malignant neoplasm of the bladder, breast, lung or thyroid.

The following examples illustrate but do not limit the invention:

EXAMPLE 1

To a solution of ethyl chloroacetate (1.226 g, 10 mmol) and 2-naphthaldehyde (1.562 g, 10 mmol) in dry tetrahydrofuran (20 ml) cooled to −78° C. under nitrogen atmosphere is added dropwise during 10 min under vigorous stirring a suspension of potassium t-butoxide (1.13 g, 10 mmol) in tetrahydrofuran (20 ml). After 30 min the yellow reaction mixture is allowed to come to room temperature, poured onto water and extracted with dichloromethane three times. The combined organic phases are dried over sodium sulfate and then concentrated under reduced pressure. The residue is submitted to column chromatography using cyclohexane/ethylacetate 97:3 as eluant to give a 3:1 trans-cis mixture of 2-carbethoxy-3-(2'-naphthyl)oxirane (1.84 g, 76% yield).

MS (m/z) 242.

NMR δ ppm (trans-isomer): 1.33 (t, J=7.1Hz, COOCH$_2$ C$\underline{H}_3$), 3.60 (d, J=1.8 Hz, H-2), 4.25 (d, J=1.8 Hz, H-3), 4.29 (m, COOC$\underline{H}_2$), 7.3–7.9 (m, 7H arom).

NMR δ ppm (cis-isomer): 0.95 (t, J=7.1Hz, COOCH$_2$ C$\underline{H}_3$), 3.88 (d, J=4.6 Hz, H-2), 3.94 (m, COOC$\underline{H}_2$), 4.41 (d, J=4.6 Hz, H-3), 7.3–7.9 (m, 7H arom).

According to the above described method (process a) the following compound can be prepared:
2-carbethoxy-3-(1'-naphthyl)oxirane;
2-carbethoxy-3-(4'-methoxy-1'-naphthyl)oxirane;
2-carbethoxy-3-(1'-methoxy-2'-naphthyl)oxirane;
2-carbethoxy-3-(5', 6', 7', 8'-tetrahydronaphth-1'-yl)oxirane;
2-carbethoxy-3-(4'-methoxy-5', 6', 7', 8'-tetrahydronaphth-1'-yl)oxirane;
2-carbethoxy-3-(5', 6', 7', 8'-tetrahydronaphth-2'-yl)oxirane;
2-carbethoxy-3-(1'-methoxy-5', 6', 7', 8'-tetrahydronaphth-2'-yl)oxirane;
2-carbethoxy-3-(4'-quinolyl)oxirane;
2-carbethoxy-3-(8'-methoxy-4'-quinolyl)oxirane;
2-carbethoxy-3-(5'-quinolyl)oxirane;
2-carbethoxy-3-(8'-methoxy-5'-quinolyl)oxirane;
2-carbethoxy-3-(3'-indolyl)oxirane, and
2-carbethoxy-3-(5'-methoxy-3'-indolyl)oxirane.

EXAMPLE 2

A solution of chloroacetonitrile (0.831 g, 11 mmol) and 2-naphthaldehyde (1.562 g, 10 mmol) in dry tetrahydrofuran (20 ml) is cooled to −78° C. under nitrogen atmosphere. Thereupon a suspension of potassium t-butoxide (1.284 g, 1.1 mmol) in tetrahydrofuran (20 ml) is added dropwise during 10 min. After 30 min the reaction mixture is allowed to come to room temperature, poured onto iced water and extracted several times with dichloromethane. The combined phases are washed with saline solution, dried over Na$_2$SO$_4$ and then evaporated under vacuum.

The residue is chromatographed on silica gel with cyclohexane/ethylacetate 9:1 thus giving pure cis-2-cyano-3-(2'-naphthyl)oxirane in 70% yield.

MS (m/z) 195.

NMR δ ppm: 3.84 (d, J=4.8 Hz, H-2), 7.4–7.9 (m, 7 H arom).

According to the above described method (process b) the following compound can be prepared:
2-cyano-3-(1'-naphthyl)oxirane;
2-cyano-3-(4'-methoxy-1'-naphthyl)oxirane;
2-cyano-3-(1'-methoxy-2'-naphthyl)oxirane;
2-cyano-3-(5', 6', 7', 8'-tetrahydronaphth-1'-yl)oxirane;
2-cyano-3-(4'-methoxy-5', 6', 7', 8'-tetrahydronaphth-1'-yl)oxirane;
2-cyano-3-(5', 6', 7', 8'-tetrahydronaphth-2'-yl)oxirane;
2-cyano-3-(1'-methoxy-5', 6', 7', 8'-tetrahydronaphth-2'-yl) oxirane;
2-cyano-3-(4'-quinolyl)oxirane;
2-cyano-3-(8'-methoxy-4'-quinolyl)oxirane;
2-cyano-3-(5'-quinolyl)oxirane;
2-cyano-3-(8'-methoxy-5'-quinolyl)oxirane;
2-cyano-8-(3'-indolyl)oxirane; and
2-cyano-8-(5'-methoxy-8'-indolyl)oxirane.

EXAMPLE 3

A solution of potassium t-butoxide (1.13 g, 10 mmol) in t-butanol (10 ml) is added to a solution of 2-naphthaldehyde (1.562 g, 10 mmol) and 2-chloroacetamide (0.935 g, 10 mmol) in t-butanol (10 ml) under an atmosphere of nitrogen at 5°–10° C. during 1 h. The mixture is stirred at 10° C. for 1 h and the alcohol is removed at 50° under reduced pressure. The residue is treated with ether and water, the separated ether layer is washed with saline solution, dried with magnesium sulfate, and evaporated to dryness. The residue is chromatographed on silica gel using cyclohexane/ethylacetate 95:5 as eluant to give pure 2-carbamoyl-3-(2'-naphthyl)oxirane in 75% yield.

MS (m/z) 213.

IR cm$^{-1}$: 3380 (NH), 1700 (amide), 1675 (amide), 1260 (epoxy).

According to the above described procedure (process c) the following compounds can be prepared:
2-carbamoyl-3-(1'-naphthyl)oxirane;
2-carbamoyl-3-(4'-methoxy-1'-naphthyl)oxirane;
2-carbamoyl-3-(1'-methoxy-2'-naphthyl)oxirane;
2-carbamoyl-3-(5', 6', 7', 8'-tetrahydronaphth-1'-yl) oxirane;
2-carbamoyl-3-(4'-methoxy-5', 6', 7', 8'-tetrahydronaphth-1'-yl)oxirane;
2-carbamoyl-3-(5', 6', 7', 8'-tetrahydronaphth-2'-yl)oxirane;
2-carbamoyl-3-(1'-methoxy-5', 6', 7', 8'-tetrahydronaphth-2'-yl)oxirane;
2-carbamoyl-3-(4'-quinolyl)oxirane;
2-carbamoyl-3-(8'-methoxy-4'-quinolyl)oxirane;
2-carbamoyl-3-(5'-quinolyl)oxirane;
2-carbamoyl-3-(8'-methoxy-5'-quinolyl)oxirane;
2-carbamoyl-3-(3'-indolyl)oxirane; and
2-carbamoyl-3-(5'-methoxy-3'-indolyl)oxirane.

EXAMPLE 4

To a solution of 2-carbethoxy-3-(2'-naphthyl)acrylonitrile (2.513 g, 10 mmol) in ethanol (20 ml) containing some drops of diluted sulfuric acid is added dropwise under stirring 1.5N sodium hypochlorite solution (10 ml). The pH of the reaction is maintained at 7 by addition of diluted sulfuric acid. After 1.5 h more 1.5N sodium hypochlorite (5 ml) is added and the reaction continued for another 0.5 h. Then the mixture is diluted with water and extracted several times with ether. The combined organic phases are dried over magnesium sulfate and evaporated to dryness. The residue is crystallized from ether-hexane to give pure 2-cyano-2-carbethoxy-3-(2'-naphthyl)oxirane in 75% yield.

MS (m/z) 269.

IR cm$^{-1}$: 2250 (nitril), 1760 (ester), 1260 (epoxy)

According to the above described procedure and starting from the appropriate compounds of formula (VI) the following compounds can be prepared (process d):

2-cyano-2-carbethoxy-3-(1'-naphthyl)oxirane;
2-cyano-2-carbethoxy-3-(4'-methoxy-1'-naphthyl)oxirane
2-cyano-2-carbethoxy-3-(1'-methoxy-2'-naphthyl)oxirane
2-cyano-2-carbethoxy-3-(5', 6', 7', 8'-tetrahydronaphth-1-yl)oxirane;
2-cyano-2-carbethoxy-3-(4'-methoxy-5', 6', 7', 8'-tetrahydronaphth-1'-yl)oxirane;
2-cyano-2-carbethoxy-3-(5', 6', 7', 8'-tetrahydronaphth-2-yl)oxirane;
2-cyano-2-carbethoxy-3-(1'-methoxy-5', 6', 7', 8'-tetrahydronaphth-2'-yl)oxirane;
2-cyano-2-carbethoxy-3-(4 -quinolyl)oxirane;
2-cyano-2-carbethoxy-3-(8 -methoxy-4'-quinolyl)oxirane;
2-cyano-2-carbethoxy-3-(5 -quinolyl)oxirane;
2-cyano-2-carbethoxy-3-(8 -methoxy-5'-quinolyl)oxirane;
2-cyano -2-carbethoxy-3-(3 -indolyl)oxirane; and
2-cyano-2-carbethoxy-3-(5 -methoxy-3'-indolyl)oxirane;

EXAMPLE 5

To a solution of 2-cyano-3-(2'-naphthyl)acrylamide (2.228 g, 10 mmol) in methanol (200 ml) cooled to about 0° C. is added dropwise in a 20 min period 30% aqueous hydrogen peroxide (14 ml) in the presence of phosphate buffer of pH 7.5. The mixture is stirred for another 1 h, then concentrated under reduced pressure to about half volume, brine is added (200 ml) and the solution extracted with dichloromethane. The organic phases are dried (Na$_2$SO$_4$) and evaporated to dryness. The residue is purified by silica gel column chromatography eluting with cyclohexane/ethylacetate 7:3 to give pure trans-2-cyano-2-carbamoyl-3-(2'-naphthyl)oxirane in 71% yield.

MS (m/z) 238.

NMR δ ppm: 4.96 (s, H-3), 7.5–8.1 (m, 7 H arom), 8.00 (bs, CONH$_2$)

Proceeding analogously and starting from the appropriate compounds of formula (VII) the following compounds can be prepared (process d):

2-cyano-2-carbamoyl-3-(1'-naphthyl)oxirane;
2-cyano-2-carbamoyl-3-(4'-methoxy-1'-naphthyl)oxirane;
2-cyano-2-carbamoyl-3-(1'-methoxy-2'-naphthyl)oxirane;
2-cyano-2-carbamoyl-3-(5', 6', 7', 8'-tetrahydronaphth-1'-yl)oxirane;
2-cyano-2-carbamoyl-3-(4'-methoxy-5', 6', 7', 8'-tetrahydronaphth-1'-yl)oxirane;
2-cyano-2-carbamoyl-3-(5', 6', 7', 8'-tetrahydronaphth-2'-yl)oxirane;
2-cyano-2-carbamoyl-3-(1'-methoxy-5', 6', 7', 8'-tetrahydronaphth-2'-yl)oxirane;
2-cyano-2-carbamoyl-3-(4'-quinolyl)oxirane,
MS m/z 225.

NMR δ ppm: 5.77 (s,1H,CHO), 7.47 (m,1H,H-6), 7.6 (d,1H,H-3), 7.69 (m,1H,H-7), 8.23 (dd,1H,H-5), 8.33 (dd,1H,H-8), 9.07 (d,1H,H-8), 9.36,9.76 (two bs,ZH,CONH$_2$);
2-cyano-2-carbamoyl-3-(8'-methoxy-3'-quinolyl)oxirane;
2-cyano-2-carbamoyl-3-(5'-quinolyl)oxirane;
2-cyano-2-carbamoyl-3-(8'-methoxy-5'-quinolyl)oxirane;
2-cyano-2-carbamoyl-3-(3'-indolyl)oxirane; and
2-cyano-2-carbamoyl-3-(5'-methoxy-3'-indolyl)oxirane.

EXAMPLE 6

A solution of 5-formyl-8-methoxyquinoline (187 mg, 1 mmol), cyanoacetamide (92 mg, 1.1 mmol) and piperidine (60 mg, 0.7 mmol) in absolute ethanol (20 ml) is heated for 4 h at 50° C. The reaction mixture is chilled to 0°–5° C., the precipitate filtered, the residue washed with ice-cooled ethanol and then dried under vacuum. Thus pure 2-cyano-3-(8'-methoxy-5'-quinolyl)acrylamide is obtained in 70% yield.

Compounds of higher purity are obtained by crystallization from ethanol.

C$_{14}$H$_{11}$N$_3$O$_2$ calcd: C 66.40 H 4.38 N 16.59 found: C 66.33 H 4.29 N 16.35

MS m/z 253.

IR cm$^{-1}$: 3600–3100 (NH), 2200 (CN), 1690 (CONH$_2$), 1610, 1590, 1560, 1510 (C=C).

According to the above described procedure, condensing an aldehyde of formula (II) with an active methylene compound of formula (VII), the other acrylic compounds of formula (VI) can be prepared.

EXAMPLE 7

Tablets each weighing 0.150 g and containing 25 mg of the active substance, can be manufactured as follows: Composition (for 10,000 tablets):

| 2-cyano-2-carbamoyl-3-(4'-quinolyl)oxirane | 250 g |
|---|---|
| Lactose | 800 g |
| Corn starch | 415 g |
| Talc powder | 30 g |
| Magnesium stearate | 5 g |

The 2-cyano-2-carbamoyl-3-(4'-quinolyl)oxirane, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 8

Capsules, each dosed at 0.200 g and containing 20 mg of the active substance can be prepared.
Composition for 500 capsules:

| 2-cyano-2-carbamoyl-3-(2'-naphthyl)oxirane | 10 g |
|---|---|
| Lactose | 80 g |
| Corn starch | 5 g |
| Magnesium stearate | 5 g |

This formulation is encapsulated in two-piece hard gelatin capsules and dosed at 0.200 g for each capsule.
We claim:

1. A compound having the general formula (IA)

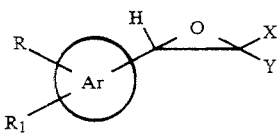

wherein
Ar is 4'-quinoline or 5'-quinoline;
each of R and $R_1$ independently is hydrogen or $C_1-C_6$ alkoxy;
one of X and Y is hydrogen, cyano, —$COOR_2$ or —$CONR_3R_4$, and the other of X and Y is cyano, —$COOR_2$ or —$CONR_3R_4$, wherein $R_2$ is $C_1-C_6$ alkyl and each of $R_3$ and $R_4$ independently is hydrogen or $C_1-C_6$ alkyl.

2. The compound according to claim 1, wherein R is hydrogen or $C_1-C_6$ alkoxy;
$R_1$ is hydrogen;
one of X and Y is —$COOR_2$ or —$CONR_3R_4$ in which $R_2$ is $C_1-C_4$ alkyl and each of $R_3$ and $R_4$ independently is hydrogen or $C_1-C_4$ alkyl, and the other one of X and Y is hydrogen or cyano.

3. The compound according to claim 1, which is selected from the group consisting of:
2-carbethoxy-3-(4'-quinolyl)oxirane;
2-carbamoyl-3-(4'-quinolyl)oxirane;
2-cyano-3-(4'-quinolyl)oxirane;
2-cyano-2-carbethoxy-3-(4'-quinolyl)oxirane;
2-cyano-2-carbamoyl-3-(4'-quinolyl)oxirane;
2-carbethoxy-3-(8'-methoxy-4'-quinolyl)oxirane;
2-carbamoyl-3-(8'-methoxy-4'-quinolyl)oxirane;
2-cyano-3-(8'-methoxy-4'-quinolyl)oxirane;
2-cyano-2 -carbethoxy-3 -(8'-methoxy-4'-quinolyl)oxirane;
2-cyano-2-carbamoyl-3 -(8'-methoxy-4'-quinolyl)oxirane;
2-carbethoxy-3-(5'-quinolyl)oxirane;
2-carbamoyl-3-(5'-quinolyl)oxirane;
2-cyano-3-(5'-quinolyl)oxirane;
2-cyano-2-carbethoxy-3-(5'-quinolyl)oxirane;
2-cyano-2-carbamoyl-3-(5'-quinolyl)oxirane;
2-carbethoxy-3-(8'-methoxy-5'-quinolyl)oxirane;
2-carbamoyl-3-(8'-methoxy-5'-quinolyl)oxirane;
2-cyano-3-(8'-methoxy-5'-quinolyl)oxirane;
2-cyano-2-carbethoxy-3-(8'-methoxy-5'-quinolyl)oxirane; and
2-cyano-2-carbamoyl-3-(8'-methoxy-5'-quinolyl)oxirane;
which, when appropriate, may be either cis- or trans-diastereomers or cis, trans-mixtures of said diastereomers.

4. A composition comprising a pharmaceutically acceptable excipient and an active substance having the following formula (IA)

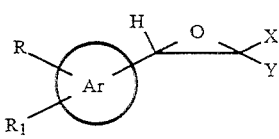

wherein
Ar is 4'-quinoline or 5'-quinoline;
each of R and $R_1$ independently is hydrogen or $C_1-C_6$ alkoxy;
one of X and Y is hydrogen, cyano, —$COOR_2$ or —$CONR_3R_4$, and the other of X and Y is cyano, —$COOR_2$ or —$CONR_3R_4$, wherein $R_2$ is $C_1-C_6$ alkyl and each of $R_3$ and $R_4$ independently is hydrogen or $C_1-C_6$ alkyl.

* * * * *